US00PP31697P2

(12) United States Plant Patent
Kordes

(10) Patent No.: US PP31,697 P2
(45) Date of Patent: Apr. 28, 2020

(54) MINIATURE ROSE PLANT NAMED 'KORPOT087'

(50) Latin Name: *Rosa hybrida*
Varietal Denomination: KORpot087

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/350,308

(22) Filed: Oct. 31, 2018

(51) Int. Cl.
*A01H 5/02* (2018.01)
*A01H 6/74* (2018.01)

(52) U.S. Cl.
USPC ..... Plt./128

(58) Field of Classification Search
USPC ..... Plt./101, 116, 121, 123, 128
See application file for complete search history.

(56) References Cited

U.S. PATENT DOCUMENTS

PP25,004 P2 10/2014 Kordes

*Primary Examiner* — Susan McCormick Ewoldt
(74) *Attorney, Agent, or Firm* — Buchanan Ingersoll & Rooney, PC

(57) ABSTRACT

A new and distinct variety of miniature rose plant, herein referred to by its cultivar name, 'KORpot087', is provided which forms in abundance on a substantially continuous basis attractive, pink-white colored blossoms. The vegetation is vigorous and the growth habit is compact. Attractive ornamental foliage is formed and good disease resistance is exhibited. The new variety is particularly well suited for providing distinctive ornamentation in the landscape.

1 Drawing Sheet

Botanical/commercial classification:
Latin name—*Rosa hybrida.*
Varietal denomination—'KORpot087'.

SUMMARY OF THE INVENTION

The new variety of *Rosa hybrida* Miniature Rose Plant of the present invention was created during 2015 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling (non-patented). The male parent (i.e., pollen parent) of the new variety was the 'KORpot028' variety (U.S. Plant Pat. No. 25,004).

The parentage can be summarized as follows:

unnamed seedling x 'KORpot028'

The seeds resulting from the above pollination were sown and small plants were obtained which were physically and biologically different from each other. Selective study resulted in the identification of a single plant of the new variety.

It was found that the new Miniature Rose Plant of the present invention possesses the following combination of characteristics:

(a) abundantly and substantially continuously forms attractive, pink-white colored blossoms,
(b) exhibits a compact growth habit,
(c) forms vigorous vegetation,
(d) forms attractive ornamental foliage, and
(e) exhibits good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the unnamed seedling (i.e., seed parent) exhibits different colored flowers and forms clusters of blooms, whereas the new variety forms blooms with single flowers. Additionally, the 'KORpot028' variety (i.e., pollen parent) exhibits dark red colored flowers, whereas the new variety exhibits pink-white colored flowers and forms a smaller flower size than the 'KORpot028' variety. Moreover, the new variety can be readily distinguished from non-parental related similar varieties. For example, the 'KORpot084" variety (U.S. Plant Pat. No. 30,573) exhibits red and pink striped colored flowers and displays less petals than the new variety, whereas the new variety exhibits pink-white colored flowers.

The new variety has been found to undergo asexual propagation in Klein Offenseth-Sparrieshoop, Germany by a number of routes, such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot087'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Marslev, Denmark while growing indoors on its own roots in 10.5 cm containers.

FIG. 1—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during October, while growing in a one-gallon container on its own roots in a greenhouse in Cochranville, Pa.

Class: Miniature Rose Plant.

Plant:

*Habit*.—Compact and rounded.

*Height*.—Approximately 30.0 cm on average.

*Width*.—Approximately 30.0 cm on average.

Branches:

*Stem color*.—Commonly near Yellow-Green Group 144A.

*Length*.—Main stems: approximately 30.0 cm on average. Secondary stems: approximately 7.0 cm on average.

*Texture*.—Glabrous.

*Thorns*.—Young thorns: sparse amount; color is commonly near Greyed-Orange Group 177B; length is approximately 4.0 mm on average; and width is approximately 2.0 mm on average at point of attachment.

Foliage:

*Young foliage color*.—Upper surface: commonly near Yellow-Green group 146A with Greyed-Purple Group 183A at the margin, and indistinguishable venation. Under surface: commonly near Yellow-Green Group 146B with Greyed-Purple Group 183A at the margin, and indistinguishable venation.

*Old foliage color*.—Upper surface: commonly near Green Group 137A with indistinguishable venation. Under surface: commonly near Green Group 138A with venation of commonly near Green Group 138B.

*Petiole*.—Upper and under surfaces: texture is smooth; color is commonly near Yellow-Green Group 144A.

*Rachis*.—Color: upper surface is commonly near Yellow-Green Group 144A, under surface is commonly near Green Group 143C.

*Stipules*.—Length: approximately 1.0 cm on average. Width: approximately 5.0 mm on average. Margin: entire to erose. Color: upper surface is commonly near Yellow-Green Group 144A, under surface is commonly near 144B.

*Leaf margin*.—Serrate.

*Glossiness of upper side of leaf*.—Semi-glossy.

Leaflets:

*Number*.—3, 5, and 7.

*Shape*.—Ovate; apex is acute; base is rounded.

*Venation pattern*.—Reticulate.

*Texture*.—Upper surface is smooth; under surface is smooth.

*Terminal leaflet*.—Length is approximately 3.7 cm on average; width is approximately 2.2 cm on average.

*Lower leaflets*.—Length is approximately 2.7 cm on average; width is approximately 2.0 cm on average.

5-*Leaflet leaf*.—Length is approximately 8.0 cm on average; width is approximately 5.5 cm on average.

Inflorescence:

*Number of blossoms per stem*.—Typically 1 bloom per stem on average.

*Number of flowers*.—About 3-5 blooms open on average on a plant at once.

*Peduncle*.—Color: commonly Yellow-Green Group 144A. Diameter: approximately 7.0 mm on average. Length: approximately 3.0 cm on average. Surface texture: glabrous. Strength: strong.

*Sepals*.—Number: commonly 5. Upper surface color and texture: covered in short pubescence; color is commonly near Yellow-Green Group 144A. Under surface color and texture: puberulent; color is commonly near Yellow-Green Group 144A. Size: length is approximately 2.2 cm on average and width is approximately 7.0 mm on average. Margin: entire with occasional extensions on two or three sepals measuring approximately 7.0 mm in length and approximately 3.0 mm in width. Shape: lanceolate; apex is acute to aristate; base is truncate or flat as it joins the receptacle.

*Bud*.—Shape: globular to pointed. Size: length is approximately 2.7 cm on average; width is approximately 2.0 cm on average. Color (when opening): commonly near Red-Purple Group 60C.

*Flower*.—Form: double, cuplike. Duration: on the plant approximately 15 days. Profile: convex, rounded. Height: approximately 3.0 cm on average. Diameter: approximately 5.0 cm on average.

*Fragrance*.—Light sweet fragrance.

*Petal*.—Number: approximately 32 on average. Drop: good. Length: inner petals are approximately 3.0 cm on average; outer petals are approximately 2.5 cm on average. Width: inner petals are approximately 2.5 cm on average; outer petals are approximately 3.5 cm on average. Shape: overall shape is broadly obovate; apex is rounded; and base is cuneate. Margin: entire. Texture: upper and under surfaces are glabrous. Color with first and fully open: upper surface is commonly near Red-Purple Group 67C with blotches creating a striping effect of near White Group 155C with basal spot of commonly near Yellow Group 4C; and under surface is commonly near Red-Purple Group 67D with basal spot of commonly near Yellow Group 4D. Color when fading: upper and under surfaces are commonly near Red-Purple Group 67C with blotches creating a striping effect of near Green-White Group 157A and a basal spot of commonly near Green-White Group 157B.

*Petaloids*.—Number: 3 per flower, on average. Color: upper surface is commonly near Red-Purple Group 67B; under surface is commonly near Red-Purple Group 67C. Length: approximately 1.0 cm on average. Width: approximately 0.5 cm on average. Texture: smooth. Margins: variable, entire to erose. Shape: variable, oblong and mostly curing inward. Apex: round. Base: cuneate.

*Stamen*.—Number: approximately 98 on average. Anthers: number is approximately 98 on average; color is commonly near is commonly near Yellow Group 11A; shape is oval; length is approximately 1.0 mm on average. Filaments: length is approximately 3.0 mm on average; color is commonly near Yellow Group 4B.

*Pistils*.—Arrangement: separate and free. Number: approximately 75. Style: color is mostly near Red-Purple Group 58B and some exhibiting a small hint of Yellow Group 11C at the base of the stigma; length is approximately 5.0 mm on average. Stigma: color is commonly near Greyed-Yellow Group 160C; diameter is approximatly 1.0 mm on average; shape is fan shaped.

*Ovary*.—Length is approximately 2.0 mm on average; width is approximately 1.0 mm on average; color is commonly near White Group 155C on average.

*Receptacle*.—Diameter is approximately 1.0 cm on average, shape is urn shaped, color is commonly near Yellow-Green Group 144A, and surface texture is smooth.

*Pollen*.—None observed.

*Hips/seed*.—None observed.

Development:

*Vegetation*.—Vigorous and strong.

*Blooming*.—Abundant and substantially continuous, reblooms well from a trim.

*Hardiness resistance to*.—Unknown.

*Diseases*.—Good resistance to *Botrytis* (*Botrytis cinerea*) and Powdery Mildew (*Sphaerotheca pannosa*) diseases under normal greenhouse growing conditions in Cochranville, Pa.

Plants of the 'KORpot087' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) abundantly and substantially continuously forms attractive, pink-white colored blossoms, (b) exhibits a compact growth habit, (c) forms vigorous vegetation, (d) forms attractive ornamental foliage, and (e) exhibits good disease resistance;

substantially as herein shown and described.

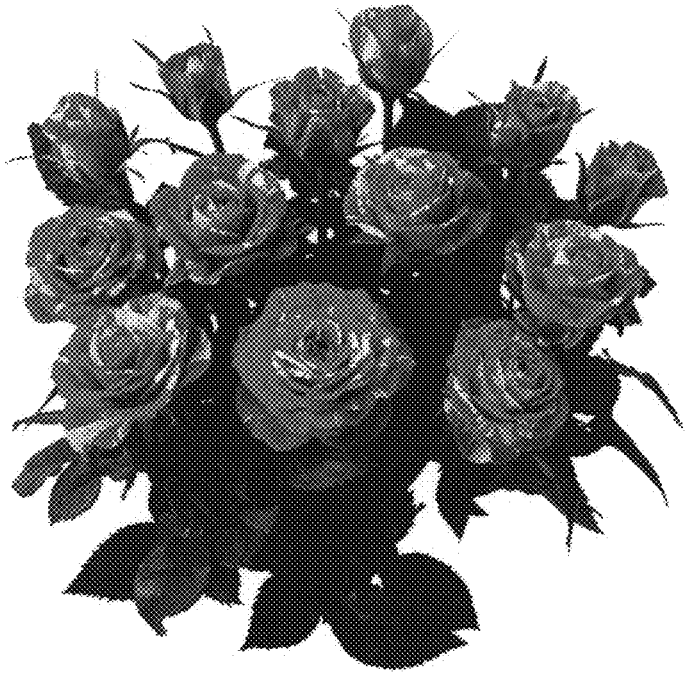

* * * * *